(12) United States Patent
Vitello (10) Patent No.: US 10,207,099 B1
(45) Date of Patent: Feb. 19, 2019

(54) CLOSURE ASSEMBLY FOR MEDICAL FITTING

(71) Applicant: Patrick Vitello, Fort Lauderdale, FL (US)

(72) Inventor: Patrick Vitello, Fort Lauderdale, FL (US)

( * ) Notice: Subject to any disclaimer, the term of this patent is extended or adjusted under 35 U.S.C. 154(b) by 855 days.

(21) Appl. No.: 14/629,085

(22) Filed: Feb. 23, 2015

Related U.S. Application Data (60) Provisional application No. 61/942,820, filed on Feb. 21, 2014.

(51) Int. Cl.
    *A61M 39/10*      (2006.01)
    *A61M 39/20*      (2006.01)

(52) U.S. Cl.
    CPC ............ *A61M 39/20* (2013.01); *A61M 39/10* (2013.01); *A61M 2039/1016* (2013.01)

(58) Field of Classification Search
    CPC .................. A61M 39/20; A61M 39/10; A61M 2039/1016
    See application file for complete search history.

(56) References Cited

U.S. PATENT DOCUMENTS

| | | |
|---|---|---|
| 732,662 A | 6/1903 | Smith |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,747,751 A | 4/1973 | Miller et al. |
| 3,872,867 A | 3/1975 | Killinger |

(Continued)

FOREIGN PATENT DOCUMENTS

| | | |
|---|---|---|
| EP | 0148116 A | 7/1985 |
| WO | WO 2017086607 | 5/2015 |

*Primary Examiner* — Lauren P Farrar (57) ABSTRACT

A closure assembly for a medical fitting including a cap, connectable in flow restricting relation to the fitting and adjustably connected to an end section having a base removably connected thereto. A primary drive assembly and a secondary drive assembly are each independently disposed in interconnecting relation between the cap and the end section. The primary and secondary drive assemblies are respectively structured to facilitate fastening and unfastening of the fitting and the cap upon oppositely directed, relative rotation between the fitting and the cap in a fastening direction and in an unfastening direction. An exterior housing may be fixedly connected to the end section and includes a hollow interior dimensioned to receive and/or retained the cap and the base therein.

14 Claims, 9 Drawing Sheets

(56) References Cited

U.S. PATENT DOCUMENTS

| | | |
|---|---|---|
| 3,905,375 A | 9/1975 | Toyama |
| 3,937,211 A | 2/1976 | Merten |
| 4,043,334 A | 8/1977 | Brown et al. |
| 4,046,145 A | 9/1977 | Choksi et al. |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,286,591 A | 9/1981 | Raines |
| 4,313,539 A | 2/1982 | Raines |
| 4,420,085 A | 12/1983 | Wilson et al. |
| 4,430,077 A | 2/1984 | Mittleman et al. |
| 4,457,445 A | 7/1984 | Hanks et al. |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,667,837 A | 5/1987 | Vitello et al. |
| 4,693,707 A | 9/1987 | Dye |
| 4,726,483 A | 2/1988 | Drozd |
| 4,743,229 A | 5/1988 | Chu |
| 4,743,231 A | 5/1988 | Kay et al. |
| 4,760,847 A | 8/1988 | Vaillancourt |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 5,009,323 A | 4/1991 | Montgomery et al. |
| 5,049,129 A | 9/1991 | Zdeb et al. |
| 5,057,093 A | 10/1991 | Clegg et al. |
| 5,135,496 A | 8/1992 | Vetter et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,295,599 A | 3/1994 | Smith |
| 5,328,466 A | 7/1994 | Denmark |
| 5,328,474 A | 7/1994 | Raines |
| 5,356,380 A | 10/1994 | Hoekwater et al. |
| 5,380,295 A | 1/1995 | Vacca |
| 5,405,339 A | 4/1995 | Kohnen et al. |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,674,209 A | 10/1997 | Yarger |
| 5,700,247 A | 12/1997 | Grimard et al. |
| 5,702,374 A | 12/1997 | Johnson |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,989,227 A | 11/1999 | Vetter et al. |
| 6,000,548 A | 12/1999 | Tsals |
| 6,021,824 A | 2/2000 | Larsen et al. |
| 6,027,482 A | 2/2000 | Imbert |
| 6,068,614 A | 5/2000 | Kimber et al. |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,375,640 B1 | 4/2002 | Teraoka |
| 6,394,983 B1 | 5/2002 | Mayoral et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,682,798 B1 | 1/2004 | Kiraly |
| 6,726,652 B2 | 4/2004 | Eakins et al. |
| 6,726,672 B1 | 4/2004 | Hanley et al. |
| 6,775,220 B2 | 6/2004 | Castellano et al. |
| 6,764,469 B2 | 7/2004 | Broselow |
| 6,821,268 B2 | 11/2004 | Balestracci |
| 6,921,383 B2 | 7/2005 | Vitello |
| 6,942,643 B2 | 9/2005 | Eakins et al. |
| 7,055,273 B2 | 6/2006 | Roshkoff |
| 7,141,286 B1 | 11/2006 | Kessler et al. |
| 7,182,256 B2 | 2/2007 | Andreasson et al. |
| 7,240,926 B2 | 7/2007 | Dalle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,588,563 B2 | 9/2009 | Guala |
| 7,594,681 B2 | 9/2009 | DeCarlo |
| 7,632,244 B2 | 12/2009 | Buehler et al. |
| 7,641,636 B2 | 1/2010 | Moesli et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 8,079,518 B2 | 12/2011 | Turner et al. |
| 8,091,727 B2 | 1/2012 | Domkowski |
| 8,137,324 B2 | 3/2012 | Bobst |
| 8,140,349 B2 | 3/2012 | Hanson et al. |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,443,999 B1 | 5/2013 | Reinders |
| D684,057 S | 6/2013 | Kwon |
| 8,512,277 B2 | 8/2013 | Del Vecchio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,930 B2 | 7/2014 | Swisher et al. |
| 8,852,561 B2 | 10/2014 | Wagner et al. |
| 8,864,021 B2 | 10/2014 | Vitello |
| 8,864,707 B1 | 10/2014 | Vitello |
| 8,864,708 B1 | 10/2014 | Vitello |
| 8,945,082 B2 | 2/2015 | Geiger et al. |
| 9,101,534 B2 | 8/2015 | Bochenko |
| 9,199,042 B2 | 12/2015 | Farrar et al. |
| 9,220,486 B2 | 12/2015 | Schweiss et al. |
| 9,220,577 B2 | 12/2015 | Jessop et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |

(56) References Cited

U.S. PATENT DOCUMENTS

| | | |
|---|---|---|
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D789,529 S | 6/2017 | Davis et al. |
| 9,687,249 B2 | 6/2017 | Hanlon et al. |
| D797,928 S | 9/2017 | Davis et al. |
| D797,929 S | 9/2017 | Davis et al. |
| 9,855,191 B1 | 1/2018 | Vitello et al. |
| D815,945 S | 4/2018 | Fischer et al. |
| D825,746 S | 8/2018 | Davis et al. |
| 2001/0034506 A1 | 10/2001 | Hirschman et al. |
| 2001/0056258 A1 | 12/2001 | Evans |
| 2002/0023409 A1 | 2/2002 | Py |
| 2002/0099334 A1 | 7/2002 | Hanson et al. |
| 2002/0101656 A1 | 8/2002 | Blumenthal et al. |
| 2002/0133119 A1 | 9/2002 | Eakins et al. |
| 2003/0146617 A1 | 8/2003 | Franko, Sr. |
| 2003/0183547 A1 | 10/2003 | Heyman |
| 2004/0064095 A1* | 4/2004 | Vitello ............... A61M 5/3134 604/111 |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0243088 A1 | 10/2008 | Evans |
| 2008/0306443 A1 | 12/2008 | Neer |
| 2009/0099552 A1 | 4/2009 | Levy et al. |
| 2009/0149815 A1 | 6/2009 | Kiel et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0088354 A1 | 4/2013 | Thomas |
| 2013/0237949 A1 | 9/2013 | Miller |
| 2014/0000781 A1 | 1/2014 | Franko, Jr. |
| 2014/0034536 A1 | 2/2014 | Reinhardt et al. |
| 2014/0069829 A1 | 3/2014 | Evans |
| 2014/0135738 A1 | 5/2014 | Panian |
| 2014/0155868 A1 | 6/2014 | Nelson et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0191633 A1 | 7/2015 | De Boer et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0319438 A1 | 11/2017 | Davis et al. |
| 2018/0001540 A1 | 1/2018 | Byun |
| 2018/0089593 A1 | 3/2018 | Patel et al. |

* cited by examiner

CLOSURE ASSEMBLY FOR MEDICAL FITTING

This is a Non-Provisional patent application that claims priority pursuant to 35 U.S.C. Section 119(e) to a prior filed Provisional patent application, namely, that having Ser. No. 61/942,820 filed on Feb. 21, 2014.

BACKGROUND OF THE INVENTION

Field of the Invention

This invention is directed to a closure assembly, which may be structured for a single use, and includes a cap capable of being connected in flow restricting relation to any one of a plurality of different medical fittings. A primary drive assembly and a secondary drive assembly are each independently disposed in interconnecting relation between the cap and an end section. The primary and secondary drive assemblies are respectively structured to facilitate a fastening and an unfastening of the fitting upon the rotation thereof, relative to the cap, in opposite fastening and unfastening directions, dependent on which of the primary and secondary drive assemblies is actively engaged.

Description of the Related Art

In the medical field, it is a relatively common procedure to for authorized medical personnel to order that a patient be given a drug or medication by injection or other procedures, including administering fluids to a patient by intravenous (IV) infusion. It is also relatively common procedure for a number of administering devices to be pre-loaded or filled by a pharmacist or other authorized personnel whether within the hospital or at another facility and location, which may be generally referred to as a filling station. However, a filling station is typically located in a remote part of the facility, relative to the patient care area where the injection is to be administered. Indeed, at large medical facilities, a filling station may resemble a factory on the hospital grounds from which drugs and other fluids are delivered to multiple nursing stations at different locations. Because of the remote location of many nurse's stations, relative to a filling station, a fluid or drug loaded administering device is very often given to another person for delivery to a nurse's station for subsequent dosing of the patient by a duly qualified nurse or other medically trained person. Also, and especially in the case where a drug has been prescribed and loaded in the administering device that is a very expensive or addictive, such as but not limited to morphine, there is a danger that the pre-loaded syringe or other administering device will be tampered with at some point, by a person seeking unauthorized access thereto. This possibility can present real danger in that if such person were to gain access to the prescribed medicine and then, inappropriately and without concern, substitute some other, unauthorized material in the syringe which looks like the actual prescribed medicine and dosage. By way of an example only, if saline solution were substituted for a dose of morphine or numerous other drugs, the result can be extremely serious. Thus, there is a problem of knowing if a sealed, preloaded syringe or other administering device has, or has not, been exposed to contamination or might otherwise have been compromised by its being tampered with. This and related types of problems have been described in one or more previously granted U.S. patents, such as U.S. Pat. No. 5,328,474.

In addition to the administration of drugs, medicine, etc., meaningful protection is required in the use of enteral feeding sets, like medical devices and accessories. As commonly recognized in the medical and related professions, the term "enteral" relates to the administration or removal of fluid in the form of liquid or gas to or from the gastrointestinal tract. Moreover, enteral connectors and/or fixtures of the type referred to herein relate to medical devices or accessories which are intended for use in enteral applications. Further, small-bore connectors for enteral application may be employed for delivery of enteral nutrition fluid from a fluid source to the patient. Additionally, it is pointed out that enteral feeding sets and extension sets may include a female fixture, wherein the source of fluid flows to the patient initially through the female fixture and to and through a cooperatively structured male enteral fixture.

Also, with regard to administering fluids to a patient by intravenous (IV) infusion, a variety of IV assemblies are known and are useful in the treatment of a number of medical conditions, as a variety of fluids and/or medicines can be administered to a patient utilizing such assemblies over a prescribed period of time and in controlled amounts. In use, a conventional IV administration assembly typically includes a reservoir or container, in the form of a bottle or more commonly, a flexible material bag, suspended on a pole or like support structure located substantially adjacent to the patient being treated, typically in an elevated relation thereto. In addition, the IV fluid flows from the supported and elevated IV bag to the patient by means of elongated, flexible tubing connected at a proximal end to the IV bag and at the other distal end, connected intravenously to the patient by way of a catheter or like structure. The IV delivery tube is also structured to connect at one end to or be interconnected with an appropriate connector, often having somewhat of a "Y" shape, that is associated with the IV assembly and in fluid communication with either the contents of the IV bag or alternatively, with the catheter in use on the patient for intravenous administration of fluids and medicines.

One such connector may be in the form of a female connector attached to the IV bag or other container and disposed in fluid communication with the contents thereof. An appropriate female connector may be in the form of a female luer connector which at least partially defines, along with a male luer connector, a "luer lock" connector assembly, as is well known in the medical profession. The male luer connector is secured to the IV delivery tubing, such as at the proximal end, and is specifically structured to be attached to the female luer connector in a manner which establishes fluid communication with contents of the IV container, and facilitates a flow of the IV fluid from the IV container through the connected male and female luer connectors. As a result, fluid flow between the patient and the interior of the IV bag is established. As is also well known, various types of valves and/or flow regulating devices may be operatively associated with the IV assembly to regulate the amount of fluid or rate of fluid delivery to the patient during the administration procedure.

In addition, known IV containers or reservoirs may incorporate an additional female luer connector or other female type connector which are disposed in fluid communication with the IV delivery tubing, such as but not limited to at the IV bag. This additional female luer connector is provided to administer additional liquid agents, such as pain medication, antibiotics, and/or other medicinal compositions, to the IV fluid being delivered to the patient. However, such an additional female luer connector may remain unused or may be accessed at a time subsequent to the initiation of the IV fluid administration, such as when additional medication or another composition is required or prescribed.

In periods of non-use, it is important to maintain a luer connector in a closed and fluid sealed condition in order to maintain sterility, and also, the integrity of the IV fluid prior to use. This is also important in order to restrict unauthorized access to the IV fluid and even to the female luer connector.

Therefore, and regardless of the known or conventional attempts to date to provide a fluid restricting closure to protect the contents of preloaded administering devices and/or enteral devices, certain problems still remain in this field of art. Accordingly, there is a need in this area for an improved, closure assembly which provides a secure and reliable fluid restricting or sealing connection to the discharge fixture or connector such as, but not limited to a female fixture associated with an enteral administering device. If any such new closure assembly were developed, it should also have additional structural and operative features which can provide a clear and reliable indication that use and/or attempted tampering with the patent administering device has occurred.

Further, if any such new closure assembly were developed it should include structural features capable of providing indications that prior use or access of the administering device has occurred. Also, any such closure assembly should be capable of use with little or no structural modification with a variety of different connectors, fixtures, administering devices, etc. Finally, if any such improved closure assembly were developed, it should also be structurally and operatively reliable, while still remaining cost effective to manufacture and assemble, in order to facilitate widespread use and acceptance throughout the medical profession.

SUMMARY OF THE INVENTION

The present invention is directed to a closure assembly structured for use with a variety of different medical fittings such as, but not limited to, pre-loaded syringes, IV bags and other fluid containers and/or delivery devices. As such, the various preferred embodiments of the closure assembly of the present invention are fastened to the exposed medical fitting in a manner which restricts fluid flow from or through the medical fitting. In addition, and as explained in greater detail hereinafter, the closure assembly may be structured as a "single use" device. When so used, the closure assembly provides evidence of prior use or access to the medical fitting by preventing a reconnection of the medical fitting to the closure assembly, once it has been removed therefrom. Therefore, one or more embodiments of the closure assembly may not include structural or operative features which provide specific observable evidence that the medical fitting has been tampered with or previously used.

Furthermore, the closure assembly is structured to facilitate its fastening and unfastening to the medical fitting when an oppositely directed, relative rotation occurs between the fitting and the closure assembly in a "fastening direction" and an "unfastening direction," respectively. As indicated above, once the medical fitting is unfastened from the closure assembly, it cannot be re-fastened or reconnected, thereby providing a clear indication that the medical fitting has been used or accessed.

In more specific terms, one or more preferred embodiments of the closure assembly include a cap structured to be fastened directly to the medical fitting in a flow restricting relation thereto. In addition, the cap is adjustably connected to an end section. A base, which may have a substantially annular configuration or be in the form of a ring, is removably connected to the end section and may be disposed in at least partially surrounding relation thereto. Further, the ring or base is disposed in supporting relation to the cap, during at least the initial assembly of the closure assembly, as well as the fastening of the fitting to the cap. One or more embodiments of the closure assembly may also include an exterior housing or sleeve fixedly secured to the end section and disposed in enclosing and possibly retaining relation to the cap and the ring or base. The exterior housing or sleeve also includes an access opening through which the medical fitting is at least partially disposed when being fastened to the cap.

Additional structural and operative features of the closure assembly include a driving mechanism which facilitates the relative rotation between the medical fitting and the cap in opposite directions. As such, the medical fitting may be rotated relative to the cap in a "fastening direction" and also, in an oppositely directed "unfastening direction." More specifically, the aforementioned driving mechanism comprises a primary drive assembly and a secondary drive assembly both independently disposable in interconnecting relation between the cap and the end section when actively engaged. Therefore, when the primary drive assembly is actively engaged, rotation of the medical fitting relative to the cap may be accomplished in the "fastening direction." In contrast, when the secondary drive assembly is actively engaged, rotation of the medical fitting relative to the cap may be accomplished in the "unfastening direction." As will be apparent, at least one preferred embodiment of the closure assembly includes an independent engagement of the primary and secondary drive assemblies, which is meant to indicate that they will not be actively engaged at the same time.

The primary drive assembly comprises a first drive segment mounted on the cap and a second drive segment connected to the end section by virtue of it being mounted on the aforementioned base or ring. Further, both the first and second drive segments include substantially equivalent drive structure preferably comprising, but not limited to, "ramp and cliff" drive structures. The first drive segment is formed on and extends along an outer circumferential edge of the cap. In cooperation therewith, the second drive segment is formed on and extends along an outer circumferential edge of the base or ring.

When the closure assembly is initially assembled, as well as prior to and during fastening of the medical fitting to the cap, the primary drive assembly is actively engaged such that the first and second drive segments are disposed in mating engagement with one another. As a result, the fitting may be fastened to the cap by exerting a rotational force thereon in a "fastening direction." The "fastening direction" may be, but is not limited to, a clockwise rotational direction. At this point, the secondary drive assembly is disengaged and will remain so, until it is desired to unfasten the medical fitting from the cap. As more fully described herein, the first and second drive segments of the primary drive assembly will become disengaged and the secondary drive assembly will become actively engaged upon an attempted unfastening of the medical fitting from the cap.

Accordingly, the secondary drive assembly comprises a third drive segment mounted on the cap and a fourth drive segment mounted on the end section. The third and fourth drive segments will be disposed in fixed, mating engagement with one another to define an active engagement of the secondary drive assembly resulting in the relative rotation between the fitting and the cap in the "unfastening direction." For purposes of clarity, the terms "first and second"

are used to refer to the drive segments of the primary drive assembly. In order to avoid confusion, the terms "third and fourth" are used to describe the drive segments of the secondary drive assembly. Such distinguishing terminology is used herein due to the cooperative disposition, operation and structuring of the primary and secondary drive assemblies.

More specifically, the first and second drive segments and the third and fourth drive segments may be substantially equivalent from a structural and operational standpoint. However, it is emphasized that the first and second drive segments of the primary drive assembly are reversely oriented from that of the third and fourth drive segments of the secondary drive assembly. As a result, relative rotation, and more specifically, rotation of the fitting relative to the cap will occur in opposite directions and are referred to herein as the aforementioned "fastening direction" and "unfastening direction."

Therefore, additional structural features of the secondary drive assembly include the third and fourth drive segments also preferably being in the form of "ramp and cliff" drive structures. Accordingly, and as emphasized above, the "ramp and cliff" drive structures of the third and fourth drive segments are reversely oriented relative to the "ramp and cliff" drive structures of the first and second drive segments. In addition, the third drive segment is formed on an interior and/or under portion of the cap. The fourth drive segment is cooperatively disposed to making Lee engage the third drive segment and as such is formed on and extends along an outer circumferential edge of the end section.

As indicated above, the cap is "adjustably connected" to the end section. Such an adjustable connection is at least partially defined by the cap being removably supported by the ring or base when the first and second drive segments of the primary drive assembly are actively engaged. As indicated, the ring or base is removably connected to the end section, preferably on an exterior thereof. When the fitting is completely and tightly fastened to the cap, by exerting a rotational force thereon in the "fastening direction, the first and second drive segments of the primary drive assembly will remain in mating, active engagement. When it is desired to unfasten the fitting from the cap, a continued forced rotation of the fitting, at least equal to a predetermined "torque limit," relative to the cap is applied in the fastening direction. Such a forced rotation will result in a disengagement of the primary drive assembly due to a disconnection and displacement of the base from the end section. As a result, the base will no longer be disposed in supporting relation to the cap. Therefore, in the absence of the supporting base, the cap will then "fall" or be displaced at least a minimal distance within the interior of the housing into a different engaging position with the end section. Moreover, such an at least minimal displacement of the cap will result in a mating, active engagement of the third and fourth drive segments of the secondary drive assembly.

Due to the reverse orientation of the primary drive assembly and the secondary drive assembly, rotation of the fitting relative to the cap in the "fastening direction" will no longer be permitted because of an engagement of the reversely oriented third and fourth drive segments of the secondary drive assembly. Therefore, active engagement of the secondary drive assembly will permit and/or facilitate rotation of the fixture, relative to the cap in the aforementioned "unfastening direction," resulting in an unfastening of the fixture from the cap. However, due to the fact that the ring or base associated with the second drive segment of the primary drive assembly has become disconnected and displaced from the end section, the medical fitting can no longer be reattached to the cap. In more specific terms, the disconnected and displaced base, will remain within the interior of the housing or sleeve in a location, which is substantially un-accessible by the cap if an attempt is made to reinsert the fitting within the housing and re-fasten it to the cap. Further, engagement of the first drive segment connected to the cap and the second drive segment connected to the now displaced base will be impossible. As a result, the medical fitting will no longer be able to rotate in the "fastening direction," relative to the cap, due to the fact that the primary drive assembly cannot be reengaged.

Therefore, in at least one preferred embodiment, the closure assembly is structured to serve as a "single use" device. Such a single use closure assembly facilitates both the fastening an unfastening thereof to a medical fitting by facilitating oppositely directed rotation of the medical fitting in a "fastening direction" and an "unfastening direction", respectively. As also indicated, one or more preferred embodiments of the closure assembly is/are effectively self-contained and may be discarded after a single use. Further, the fastening of the medical fitting to the cap results in a controlled or predetermined "tightness" which may be preferred by personnel handling the closure assembly. The continued forced rotation of the fitting relative to the cap to accomplish an engagement of the secondary drive assembly and a disengagement of the primary drive assembly can be based on a predetermined and/or pre-established "torque limit." It is also noted that the "torque limit" may vary dependent, at least in part upon the structural features of the various components of the closure assembly. As a result, the exertion of a rotational force on the medical fitting, equal to or greater than the "torque limit," will serve to disengage the primary drive assembly and engage the secondary drive assembly.

Additionally, the fastening of the closure assembly to a medical fitting can be accomplished in another embodiment and/or mode of operation wherein the primary drive mechanism is structured to disengage, so that when installation is complete, the device is structured to spin freely. In this embodiment, the user would know installation is complete by virtue of the spinning of the device, and would not need to judge when the fitting is completely and tightly fastened, and further, operating the device should serve to standardize the installation torque, the removal torque and the seal strength of the connection.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As represented in the accompanying Figures, the present invention is directed to a closure assembly, generally indicated as 10, structured to be fastened, in flow restricting relation, to a medical fitting, generally indicated as 100. As emphasized throughout, the medical fitting 100 is intended to be representative of a number of different medical fittings, fixtures, etc. In turn, different medical fittings 100 may be associated with a variety of different medical devices such as, but not limited to, a preloaded syringe, an IV bag or container, or other fluid supply or fluid source of the type commonly used in the medical profession.

As will be explained in greater detail hereinafter, the closure assembly 10 may be structured to be a "single-use" device, wherein the fitting 100 is prevented from being refastened to the closure assembly 10, once it has been removed therefrom, as described in greater detail in FIGS. 1-4. The closure assembly 10 provides evidence of prior use or access to the medical fitting 100, by being structured to prevent the reconnection of the medical fitting 100 to the closure assembly 10, once it has been removed therefrom. However, one or more embodiments of the closure assembly 10 may not include structural or operative features which provide observable evidence that the medical fitting 100 has been previously used, other than the inability to reconnect the medical fitting 100 to the closure assembly 10.

With reference now to FIGS. 1-4, there is shown a closure assembly 10 in accordance with the present invention which is illustrated in various stages of assembly, fastening and unfastening to the medical fitting 100. Accordingly, the closure assembly 10 includes a cap 12, a base 14 and an end section 16, the latter of which is represented in detail in FIG. 6A. The base 14 may be in the form of a ring and/or otherwise have a substantially annular configuration. Also, the ring or base 14 is removably connected to the exterior of the upper end 16' of the end section 16. When so connected, the base 14 will be at least initially disposed in supporting relation to the cap 12. In one or more preferred embodiments, the closure assembly 10 may also include an outer sleeve or housing 18 disposed in at least partially enclosing and/or retaining relation to the cap 12 and base 14. When included as part of the closure assembly 10, the housing 18 and the end section 16 are fixedly attached. As a result, and as more fully explained hereinafter, the cap 12 and the base 14 are removably disposed within the interior of the housing 18. As also represented, the housing 18 includes an access opening 20 dimensioned, disposed and configured to facilitate at least partial insertion of a portion 102 and nozzle or port 104 into the interior of the housing 18 in an accessible, fastening relation to the cap 12.

Figure 1:
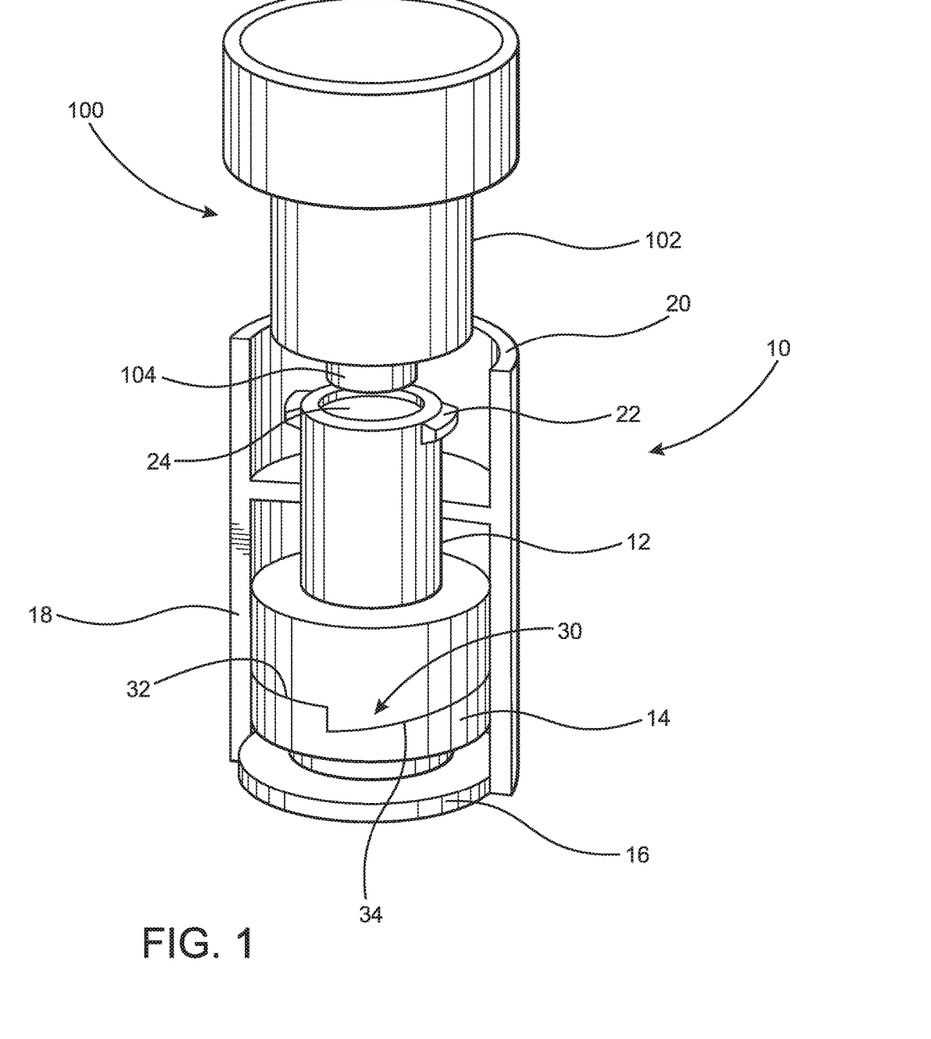
FIG. 1 is a perspective view in exploded form of a closure assembly in accordance with the present invention illustrating a position in which it is to be fastened to a medical fitting.
Figure 4:
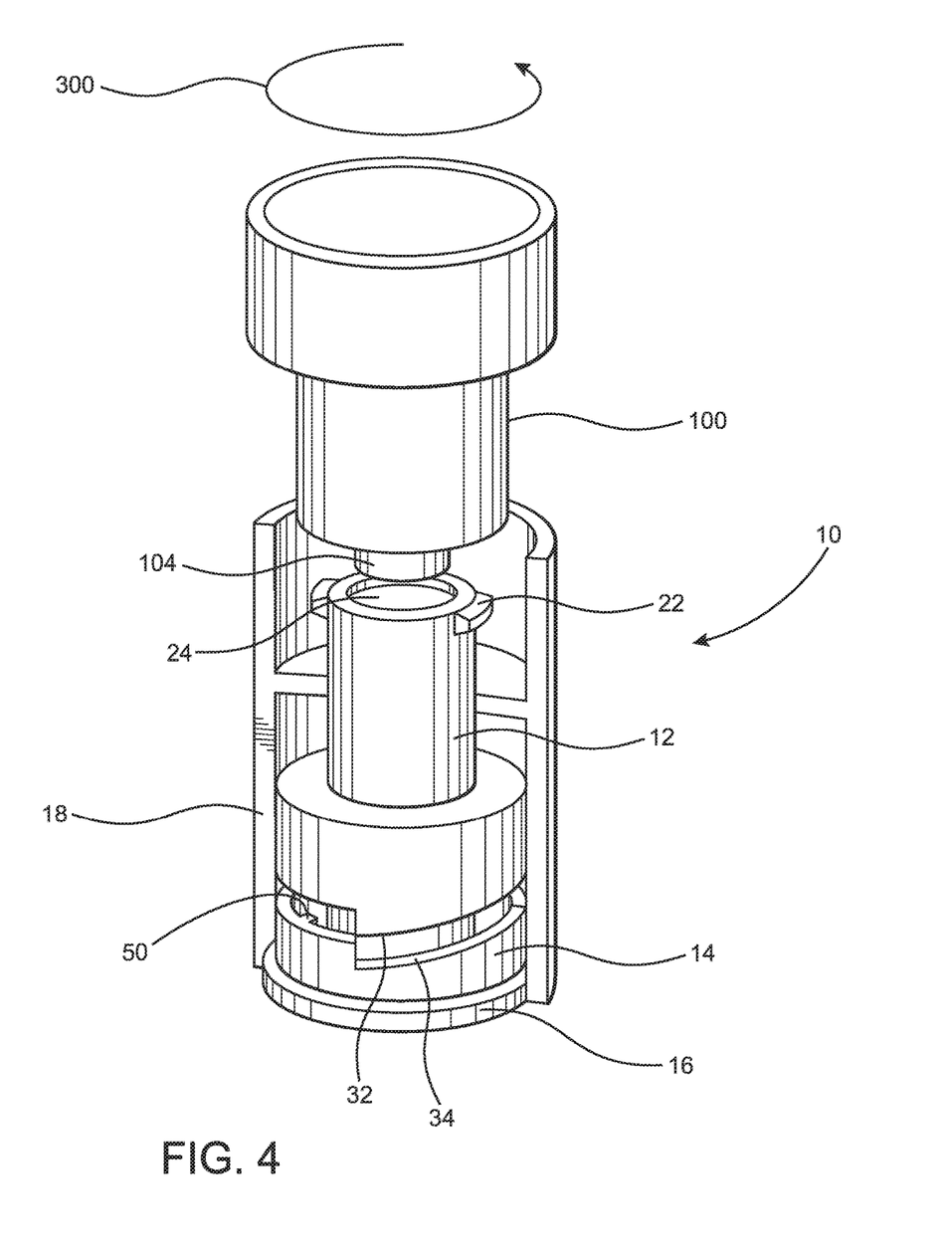
FIG. 4 is also a perspective view of the embodiment of FIGS. 1-3, but illustrating the medical fitting as having been completely removed from the closure assembly.
Figure 5:
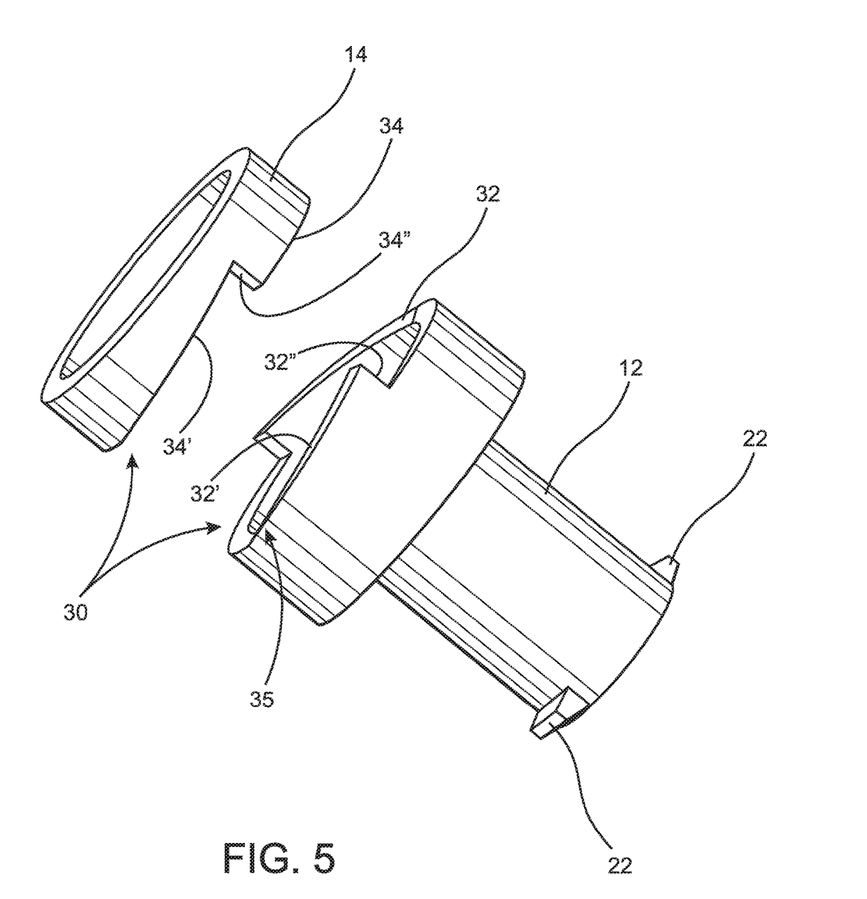
FIG. 5 is a perspective view in exploded form of operative components of a primary drive assembly of the closure assembly represented in the embodiments of FIGS. 1-4.

As emphasized throughout, the medical fitting 100 may assume a variety of different dimensions, configurations and structures and may be associated with different medical devices commonly used in the medical profession. However, for purposes of clarity a fastening of the fitting 100 to the cap 12 may occur by a relative rotation there-between. Therefore, one embodiment of the cap 12 may include outwardly projecting ribs or like structures 22, perhaps best shown in FIGS. 1 and 4, which are dimensioned to fit within the interior of the end portion 102 of the fitting 100. As a result, rotation of the fitting 100 relative to the cap 12 may result in a threaded or otherwise fastened relation therebetween based on and interaction of the ribs 22 with cooperatively disposed and structured connecting features on the interior surface or other location of the end portion 102. As also represented in FIGS. 1 and 4, the flow restricting relation between the cap 12 and the fitting 100 may be accomplished by an insertion of the nozzle or port structure 104 into the interior 24 of the corresponding portion of the cap 12. Engagement between the port structure 104 and the interior 24 may be accomplished by a known Luer type connector or other appropriate connector structures.

Additional structural and operative features of the closure assembly 10 are represented in FIGS. 5-10. More specifically, and as perhaps best shown in FIG. 5, the closure assembly 10 includes a primary drive assembly, generally indicated as 30, comprising a first drive segment 32 and a second drive segment 34. The first drive segment 32 is formed on and extends along an outer circumferential edge, generally indicated as 35 of the cap 12. In cooperation therewith, the second drive segment 34 is formed on and extends along an outer circumferential edge of the ring or base 14. The first and second drive segments 32 and 34 may have substantially equivalent operative features. In at least one embodiment, the first and second drive segments 32 and 34 each comprise a "ramp and cliff" drive structure. Such ramp and cliff drive structures of first drive segments 32 include successively disposed ramps 32' and cliffs 32" disposed in contiguous relation to one another. Such ramp and cliff drive structures of second drive segment 34 include successively disposed ramps 34' and cliffs 34" disposed in contiguous relation to one another. As such, fixed mating engagement between the first and second drive segments 32 and 34 will result in the medical fitting 100 being permitted to rotate, relative to the cap 12, in only one "fastening direction". The one "fastening direction," which can be, but does not have to be, in a clockwise direction, as schematically represented by directional arrow 200 in FIG. 2. It is noted briefly herein that the "unfastening direction" is schematically represented in FIG. 4 as 300, which will be described more in detail below.

Figure 2:
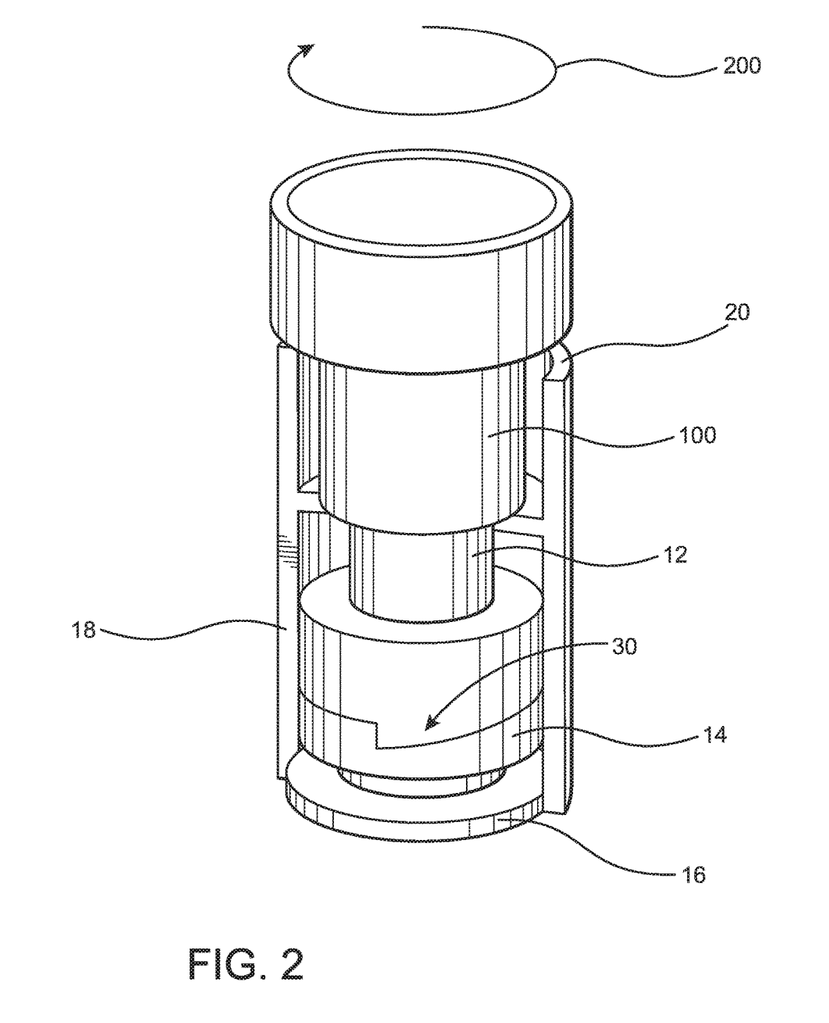
FIG. 2 is a perspective view of the embodiment of FIG. 1, wherein the closure assembly is connected in flow restricting engagement to the medical fitting.

Moreover, when the first and second drive segments 32 and 34 are in mating engagement, as represented in FIGS. 1 and 2, the primary drive assembly 30 is actively engaged. Attempted rotation of the fitting 100 and the now connected cap 12 in the opposite direction to the fastening direction 200 will result in a "slippage" or sliding between the cap 12 and the supporting base or ring 14. Therefore, the primary drive assembly 30, when actively engaged as represented in FIGS. 1-2, only permits rotation of the fastened fitting 100 and cap 12 in the one "fastening direction" 200.

Figure 3:
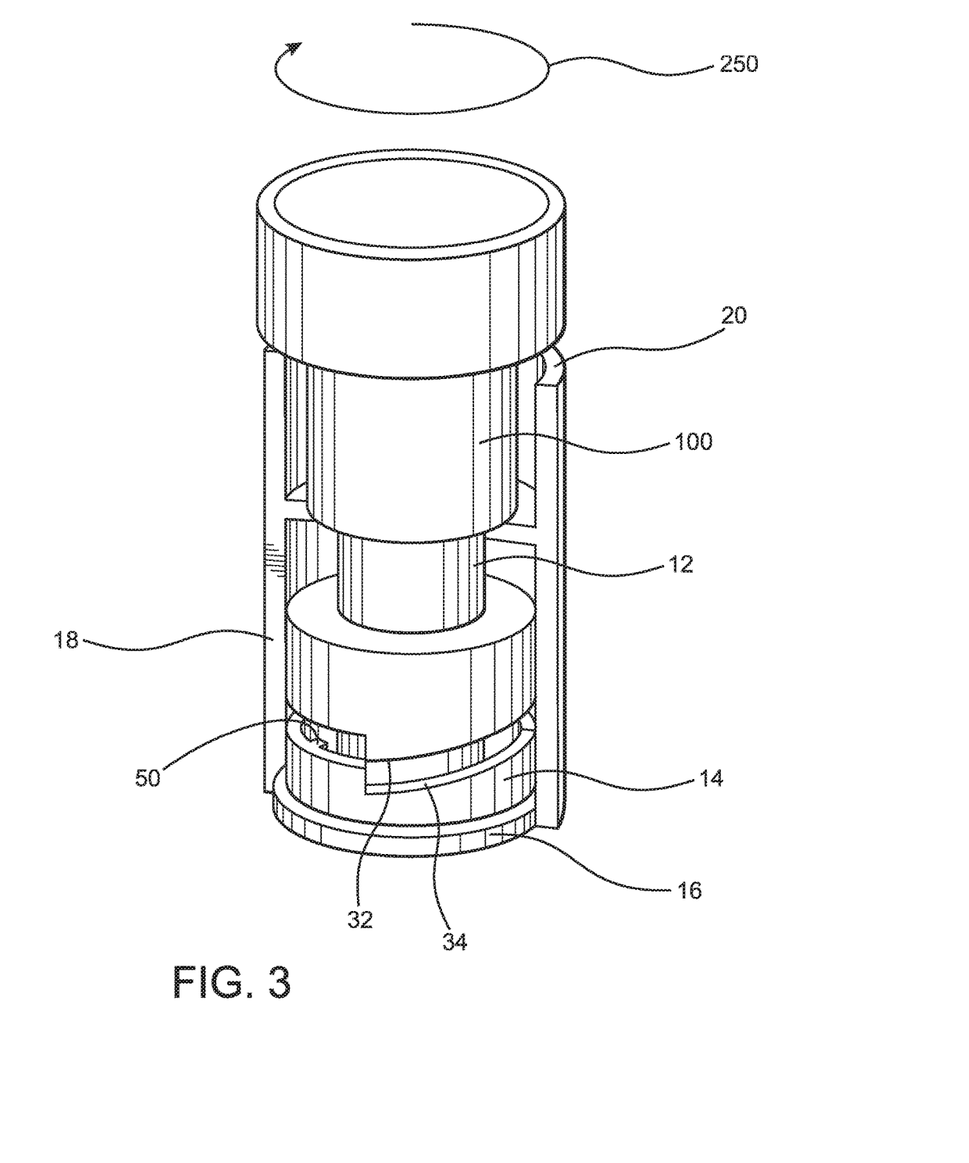
FIG. 3 is a perspective view of the embodiment of FIGS. 1 and 2, wherein the medical fitting is being unfastened from the closure assembly.
Figure 9:
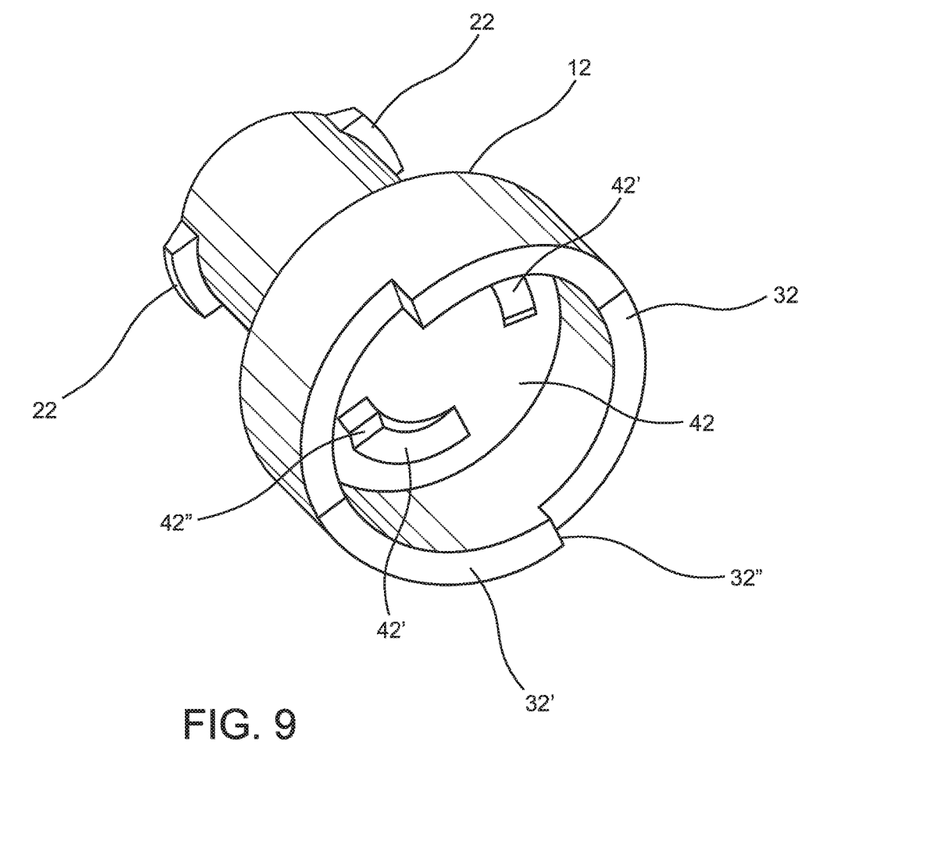
FIG. 9 is a bottom, interior, perspective view of a cap component of the embodiment of the closure assembly as represented in FIGS. 1-5.
Figure 10:
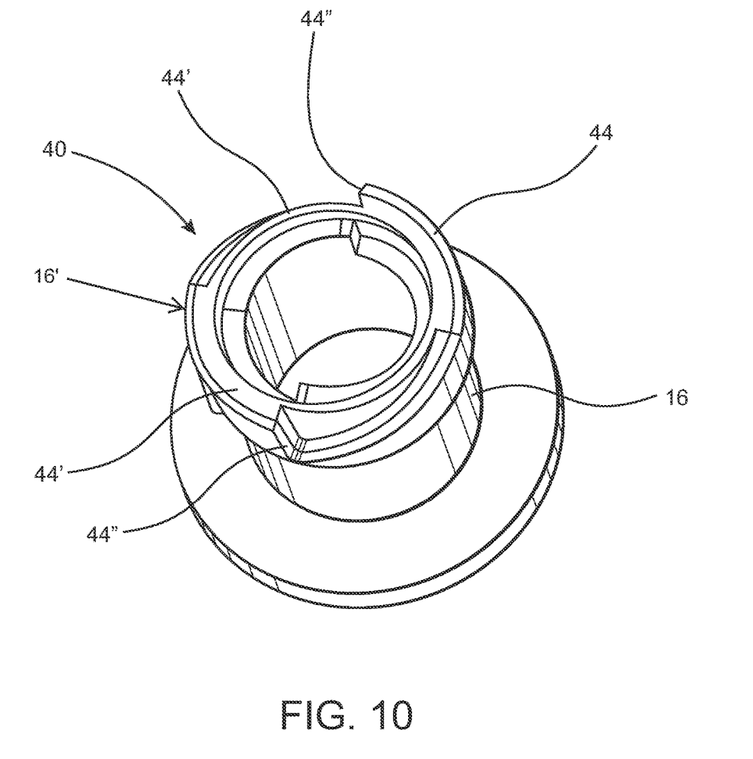
FIG. 10 is a perspective view of an end section component of the embodiment of the closure assembly as represented in FIGS. 1-4 and 6A.

With reference now to FIGS. 9-10, the closure assembly 10 also includes a secondary drive assembly, generally indicated as 40, comprising a third drive segment 42 and a fourth drive segment 44. The third drive segment 42 is mounted on an interior of the cap 12 and the fourth drive segment 44 is mounted on the outer or upper end 16' of the end section 16. In addition, the third and fourth drive segments 42 and 44 may be substantially equally structured and cooperatively disposed to define a mating engagement therebetween. Further, the third and fourth drive segments may each comprise a "ramp and cliff" drive structure operationally similar to, but structurally distinguishable from, the "ramp and cliff" drive structures of the first and second drive segments 32 and 34, respectively. Accordingly, the third drive assembly 42 may include a plurality of ramps 42' disposed in contiguous, successive relation to correspondingly disposed cliffs 42". Similarly, the fourth drive segment 44 includes one or more ramps 44' disposed in successive, contiguous relation to one or more cliffs 44". Due to the operative features of the ramp and cliff drive structures of the third and fourth drive segments 42 and 44, relative rotation between the medical fitting 100 and the cap 12 is only permitted in the "unfastening direction" 300, as schematically represented in FIG. 4. Therefore, the secondary drive assembly 40, when actively engaged as represented in FIGS. 3-4, only permits rotation of the fitting 100, relative to the cap 12, in the opposite "unfastening direction" 300, which is opposite to the "fastening direction" 200.

It is further emphasized that while the first and second drive segments 32 and 34 are structurally and/or operationally similar to the third and fourth drive segments 42 and 44, the first and second drive segments 32 and 34 are "reversely oriented" to the third and fourth drive segments 42 and 44. This "reversed orientation" of the respective drive segments of the primary drive assembly 30 and the secondary drive assembly 40, when actively engaged as respectively represented in FIGS. 1-2 and FIGS. 3-4 permits relative rotation between the fitting 100 and the cap 12 in two opposite directions. Accordingly, active engagement of the primary drive assembly 30 facilitates rotation of the fitting 100 relative to the cap 12 in the "fastening direction" 200, until a tight connection therebetween is accomplished. Due to the fact that the primary drive assembly and the secondary drive assembly 40 are not engaged at the same time, an attempted rotation of the medical fitting 100 relative to the cap 12, in an opposite direction to that of the fastening direction 200, will result in a "slippage" between the fitting 100 and the cap 12. Therefore, as long as the primary drive assembly 30 remains engaged as represented in FIGS. 1-2, the fitting 100 cannot be unfastened from the cap 12 by exerting an oppositely directed rotating force in an unfastening direction 300 as represented in FIG. 4.

When initially assembled and ready to be fastened to fitting 100, as represented in FIG. 1, the closure assembly 10 has the primary drive assembly 30 engaged. Attachment or fastening of the fitting 100 is accomplished by an at least partial insertion of the end portion 102 and/or port 104 through the access opening 20 of the housing 18. This will place the connecting tabs 22 in interactive relation with a cooperative connector structure located within the interior of the end portion 102. Continued rotation in the fastening direction 200, which can be, but does not have to be in a clockwise direction, will result in a fastening of the fitting 100 to the cap 12. In use, the fitting 100 will be continually rotated in the fastening direction 200 in one or more embodiments until there is a tight, connection completed between the fitting 100 and the cap 12, as represented in FIG. 2. At this stage of use, the primary drive assembly 30 is still engaged.

Yet another operative procedure associated with the same structural features of the illustrated closure assembly 10, and of the primary drive assembly 30 and the secondary drive assembly 40 in particular, would involve a rotation of the fitting 100, relative to the cap 12 in the fastening direction until a completed, tight fit there between has been obtained. Thereafter, a continued, forced rotation of the fitting 100 relative to the cap 12 would cause a disengagement of the primary drive assembly 30 and an engagement of the secondary drive assembly 40. With the primary drive assembly 30 disengaged, and subsequent to the additional forced rotation of the fitting 100 relative to the cap 12, the fitting 100 would freely spin or rotate, without substantial resistance, due to the orientation of the drive structures of the drive segments 32 and 34 of the primary drive assembly 30. Similarly, the drive segments and/or drive structures 42 and 44 of the secondary drive assembly, being reversely oriented to those of the primary drive assembly 30, would not restrict or prevent the aforementioned free spinning and/or rotation of the fitting 100 relative to the cap 12, even though the secondary drive assembly would be engaged. As a result of this feature, the user would know when installation and/or connection of the fitting 100 relative to the cap 12 is complete, by virtue of the free spinning or rotation of the fitting 100 relative to the cap 12. In turn, the user would not need to judge when the fitting 100 is completely and tightly fastened. Further, and as described subsequently herein, connecting the fitting 100 to the closure assembly 10 in this manner could serve to standardize the installation torque, the removal torque (torque limit) as well as the seal strength of the resulting connection between the fitting 100 and the closure assembly 10.

In order to use or have access to the fitting 100, an opposite rotational force is exerted in an unfastening direction 300, as represented in FIG. 4, so as to be unfastened from the cap 12. However, due to the orientation of the first and second drive segments 32 and 34 of the primary drive assembly 30, rotation of the fitting 100 in the opposite, unfastening direction 300 will result in the aforementioned "slippage" or relative movement between the cap 12 and the base or ring 14, as long as the primary drive assembly 30 remains actively engaged. Therefore, the disengagement of the primary drive assembly 30 and subsequent or almost concurrent engagement of the secondary drive assembly 40 is accomplished in a manner which will be described with primary reference to FIGS. 2, 3, 6 and 6A.

More specifically, when the primary drive assembly 30 is engaged as perhaps best shown in FIG. 2, the base or ring 14 will be removably and "loosely" supported on the exterior of the outer or upper end 16' of the end section 16. This is accomplished by the provision of an attachment structure, such as one or more attachment tabs or fingers 50, which are perhaps best shown in FIG. 6, that extend outwardly from an interior surface 15 of the ring or base 14. When the primary drive assembly 30 is engaged, the attachment members or tabs 50 will be disposed in supported engagement on the fourth drive segment as represented in phantom lines in FIG. 6A. When so positioned, one or both of the tabs 50 will be loosely disposed in abutting relation to a corresponding cliff 44". Accordingly, and with primary reference again to FIG.

Figure 8:
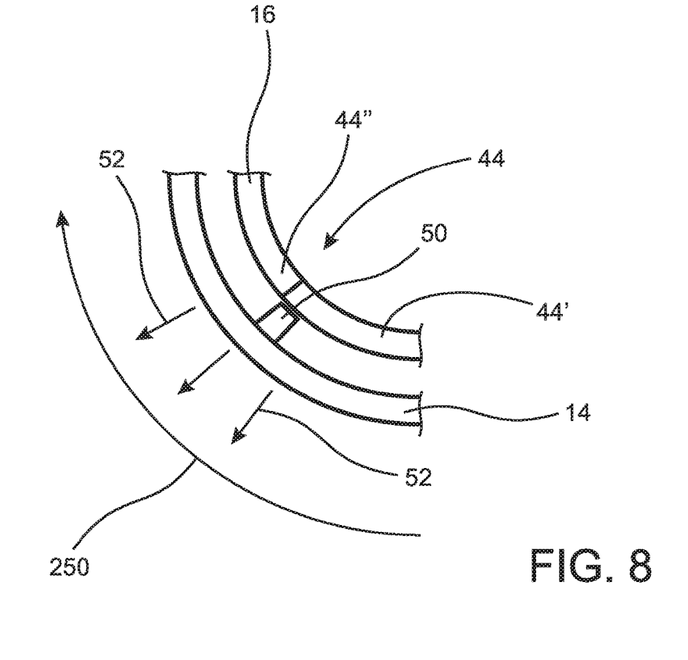
FIG. 8 is a detailed view in partial cutaway of the embodiment of FIG. 7 representing a disengagement of the primary drive assembly.

3, when the fitting 100 is disposed in a completed, tight fastening connection with the cap 12, a continued forced rotation 250 may be exerted on the fitting 100. This continued, supplementary, forced rotation 250, in the fastening direction 200, will result in a forced removal of the one or more attachment tabs 50, away or outwardly from the fourth drive segment 44 of the end section 16, as represented in FIG. 8.

Figure 6:
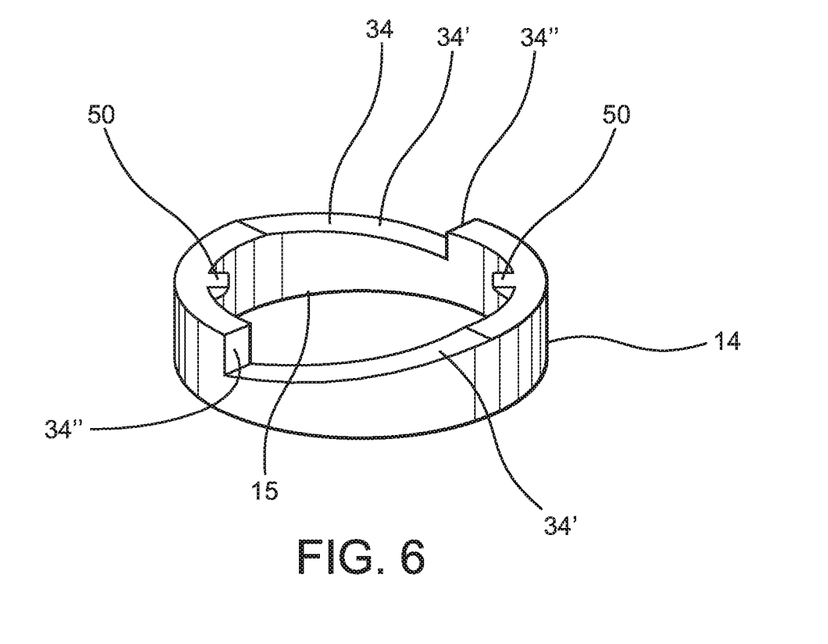
FIG. 6 is a detailed perspective view of an operative component of the primary driving assembly of the embodiments of FIGS. 1-5.
Figure 6A:
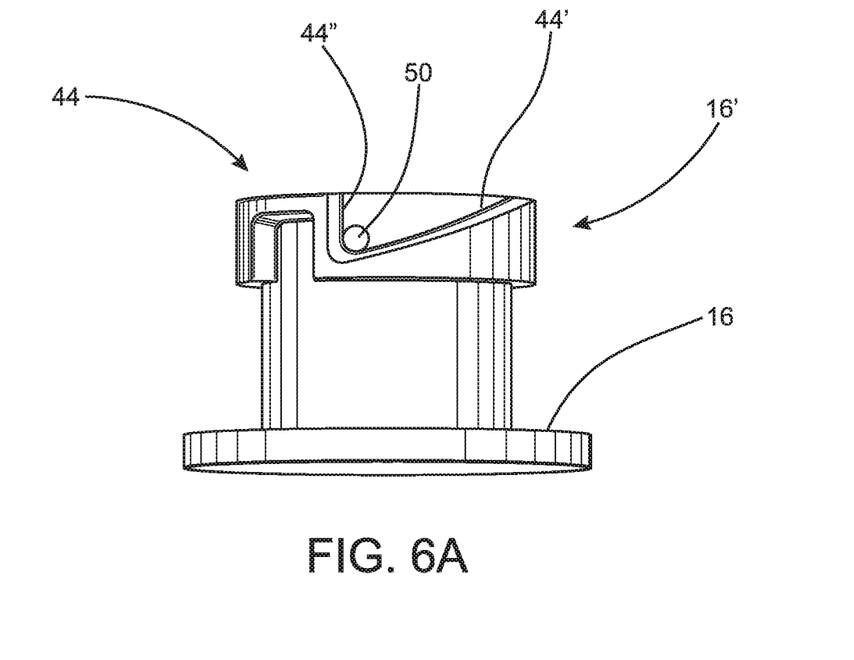
FIG. 6A is a side view of an end section of the embodiments of FIGS. 1-4.
Figure 7:
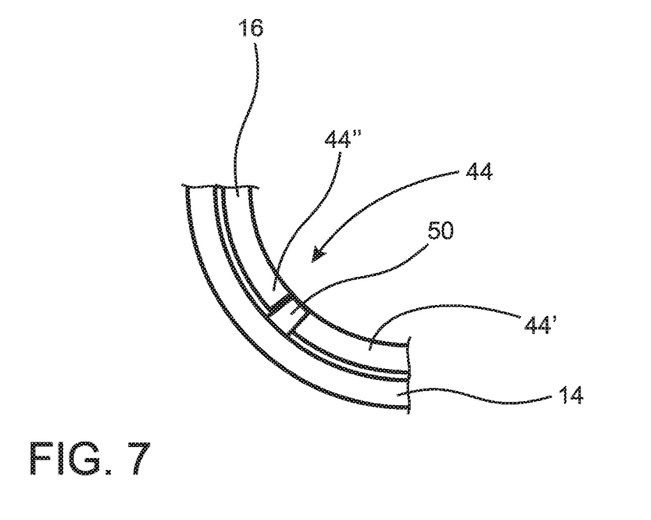
FIG. 7 is a detailed view in partial cutaway of interacting components of primary and secondary drive assemblies of the embodiments of FIGS. 1-6A.

With reference now to FIG. 7, and as set forth above, while the primary drive assembly 30 remains actively engaged, the attachment members 50 of the ring or base 14 will remain in supported engagement on the fourth drive segment 44 thereby serving to support the ring or base 14 on the outer end 16' and maintain the primary drive assembly 30 engaged, as also represented schematically in FIG. 6A. However, an exertion of a supplementary or increased rotational force 250 in the fastening direction 200 will result in an at least minimal deformity or flexing of the ring 14, and a radially outward displacement of the attachment tabs 50 away from the fourth drive segment 44, as schematically represented in FIG. 8. This, in turn, will result in a disconnection of the base or ring 14 from the outer or upper end 16' of the section 16 and a "falling" of or positioning of the base or ring 14 towards and into engagement with the bottom of the end section 16, as clearly represented in FIGS. 3 and 4. Concurrently, a disconnection and displacement of the ring 14, upon the exertion of the increased or supplemental force 250 in the fastening direction 200, will result in the separation of the first and second drive segments 32 and 34 and a resulting displacement or "falling" of the cap 12 downwardly towards the interior bottom of the end section 16. This downward falling or displacement will result in an engagement between the third and fourth drive segments 42 and 44 of the secondary drive assembly 40. Therefore, disengagement of the primary drive assembly 30 will result in a subsequent and almost concurrent engagement of the secondary drive assembly 40, as explained above.

As indicated above, at least one preferred embodiment of the closure assembly 10 includes the one or more attachment members 50 "loosely" disposed on the fourth drive segment 44, without being fixedly attached thereto, as represented in FIG. 6A. However, another embodiment of the structure may include the one or more attachment members 50 being fixedly or otherwise secured to an appropriate portion of the end section 16, wherein the one or more attachment members 50 may be formed of a frangible material. Accordingly, in this latter embodiment the exertion of the supplemental force 250 in the fastening direction 200 will result in a breakage of the one or more attachment members 50, and the disconnection and displacement of the ring 14 and a disengagement of the primary drive assembly 30, in the manner set forth above.

Due to the fact that the first and second drive segments 32 and 34 are reversely oriented, relative to the third and fourth drive segments 42 and 44, engagement of the secondary drive assembly 40 and disengagement of the primary drive assembly 30 will result in the ability of the medical fitting 100 to be rotated in the unfastening direction 300, which as indicated previously herein, is opposite to the fastening direction 200. Continued rotation of the fitting 100, relative to the cap 12 in the unfastening direction 300, will result in the ability to completely remove the fitting 100 from the cap 12, and allow it to be removed from the interior of the housing or sleeve 18. As also indicated above, a reattachment of the fitting 100 to the cap 12 will not be possible due, at least in part, to the fact that the ring or base 14 remains detached from the exterior of the end section 16. Therefore, engagement between the first and second drive segments 32 and 34 cannot be accomplished and rotation of the medical fitting 100 in a fastening direction 200 cannot occur. Consequently, a reconnection of the fitting 100 to the cap 12 will not be possible, as should be apparent.

Accordingly, the closure assembly 10 may be structured to provide a single use closure assembly to be used with a variety of different medical fittings and which may establish a flow restricting connection therebetween. Further, the closure assembly 10 may provide evidence of use or access to the fitting 100 by preventing reattachment thereof to the cap 12 and/or closure assembly 10.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A closure assembly for a medical fitting comprising:
a cap connectable in flow restricting relation to the fitting,
an end section, said cap adjustably connected to said end section,
a primary drive assembly and a secondary drive assembly each independently and separately disposed in active engagement and interconnecting relation between said cap and said end section,
said primary drive assembly, when in said active engagement, structured to facilitate fastening of the fitting to said cap upon relative rotation therebetween in a fastening direction,
said secondary drive assembly, when in said active engagement, structured to facilitate unfastening of the fitting to said cap upon rotation therebetween in an unfastening direction, and
said fastening direction and said unfastening direction being in opposite directions.

2. The closure assembly as recited in claim 1 wherein said primary drive assembly comprises a first drive segment mounted on said cap and a second drive segment connected to said end section, said first and second drive segments disposed in a fixed, mating engagement to define said active engagement upon said relative rotation in said fastening direction.

3. The closure assembly as recited in claim 2 wherein said first drive segment is mounted on an exterior of said cap; said second drive segment including a base connected to an outer end of said end section in removable mating engagement with said first drive segment.

4. The closure assembly as recited in claim 3 wherein said first drive segment is formed on and extends along an outer circumferential edge of said cap.

5. The closure assembly as recited in claim 4 wherein said second drive segment is formed on and extends along an outer circumferential edge of said base.

6. The closure assembly as recited in claim 2 wherein said first and second drive segments each comprise a ramp and cliff drive structure.

7. The closure assembly as recited in claim 2 wherein said secondary drive assembly comprises a third drive segment mounted on said cap and a fourth drive segment mounted on said end section, said third and fourth drive segments disposed in fixed mating engagement to define said active engagement upon said relative rotation in said unfastening direction and upon said disengagement of said primary drive assembly.

8. The closure assembly as recited in claim 7 wherein said third drive segment is formed on an interior of said cap.

9. The closure assembly as recited in claim 8 wherein said fourth drive segment is formed on and extends along an outer circumferential edge of an outer end of said end section.

10. The closure assembly as recited in claim 7 wherein said third and fourth drive segments each comprise a ramp and cliff drive structure.

11. The closure assembly as recited in claim 7 wherein said first and second drive segments including a substantially reversed orientation from said third and fourth drive segments.

12. The closure assembly as recited in claim 1 further comprising a housing, said end section fixedly secured to said housing and said cap movably disposed within said housing in an accessible location to the fitting.

13. The closure assembly as recited in claim 1 wherein said adjustable attachment of said cap and said end section comprises relative movement between said cap and said end section upon a disengagement of said primary drive assembly and an engagement of said secondary drive assembly.

14. The closure assembly as recited in claim 13 wherein said disengagement of said primary drive assembly is at least partially defined by a forced rotation of the fitting and said cap in said fastening direction, subsequent to said fastening of the fitting and said cap.

\* \* \* \* \*